(12) United States Patent
Khanna

(10) Patent No.: US 8,206,425 B2
(45) Date of Patent: Jun. 26, 2012

(54) CRANIAL FIXATION DEVICE

(75) Inventor: Rohit Kumar Khanna, Daytona Beach, FL (US)

(73) Assignee: Neurovention, LLC, Daytona Beach, FL (US)

(*) Notice: Subject to any disclaimer, the term of this patent is extended or adjusted under 35 U.S.C. 154(b) by 364 days.

(21) Appl. No.: 12/462,223

(22) Filed: Jul. 31, 2009

(65) Prior Publication Data

US 2011/0028973 A1  Feb. 3, 2011

(51) Int. Cl.
*A61B 17/04* (2006.01)
*A61B 17/84* (2006.01)
*A61F 2/08* (2006.01)

(52) U.S. Cl. .................................................. 606/324

(58) Field of Classification Search .................. 606/252, 606/282, 903, 74, 326, 328, 324
See application file for complete search history.

(56) References Cited

U.S. PATENT DOCUMENTS

| | | |
|---|---|---|
| 5,578,036 A | 11/1996 | Stone et al. |
| 5,707,373 A | 1/1998 | Sevrain et al. |
| 5,800,436 A | 9/1998 | Lerch |
| 5,916,200 A | 6/1999 | Eppley et al. |
| 5,916,217 A | 6/1999 | Manthrop et al. |
| 6,379,363 B1 | 4/2002 | Herrington et al. |
| 6,485,493 B1 | 11/2002 | Bremer |
| 6,589,244 B1 | 7/2003 | Sevrain et al. |
| 6,685,707 B2 | 2/2004 | Roman et al. |
| 6,755,834 B2 | 6/2004 | Amis |
| 7,048,737 B2 | 5/2006 | Wellisz et al. |
| 7,361,178 B2 | 4/2008 | Hearn et al. |
| 7,387,633 B2 | 6/2008 | Ahmad et al. |

*Primary Examiner* — Thomas C. Barrett
*Assistant Examiner* — Sameh Boles

(57) ABSTRACT

A cranial fixation system and method are provided. The system includes two heads slidably connected with telescopic extensions and a spring or an elastomeric flexible component. The two heads are maintained in a distracted position by a locking mechanism until ready for cranial implantation. Once implanted, the locking mechanism is disengaged, thereby allowing the heads to compress towards each other by the spring and approximate the cranial bone flap to the skull.

23 Claims, 26 Drawing Sheets

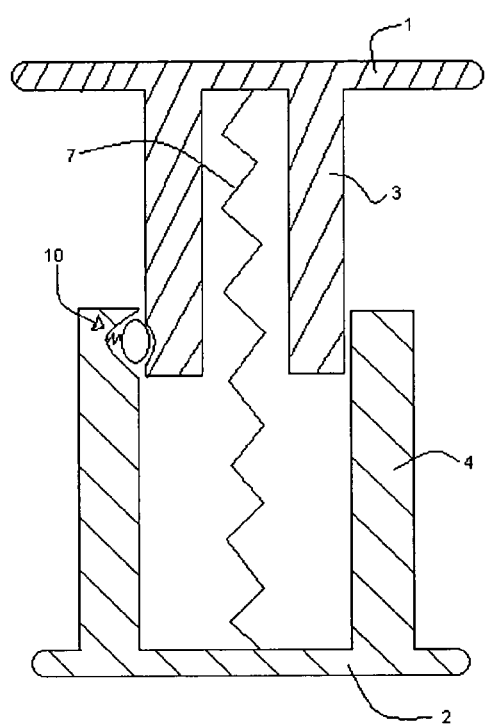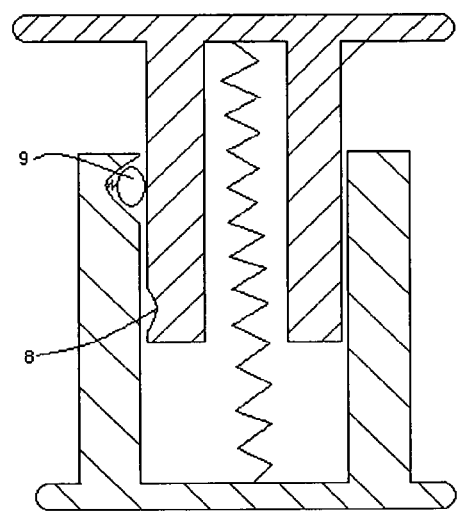
FIG. 6
FIG. 7

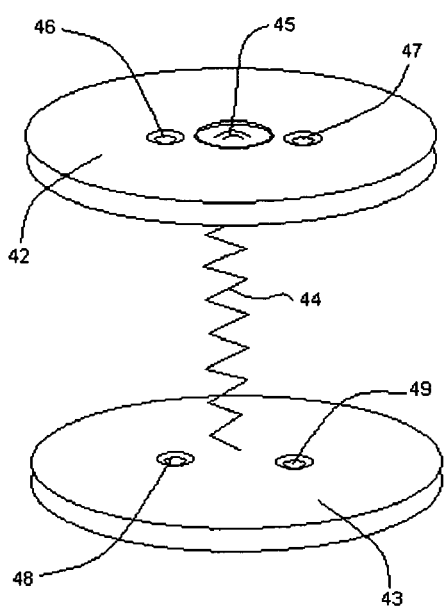
FIG. 26
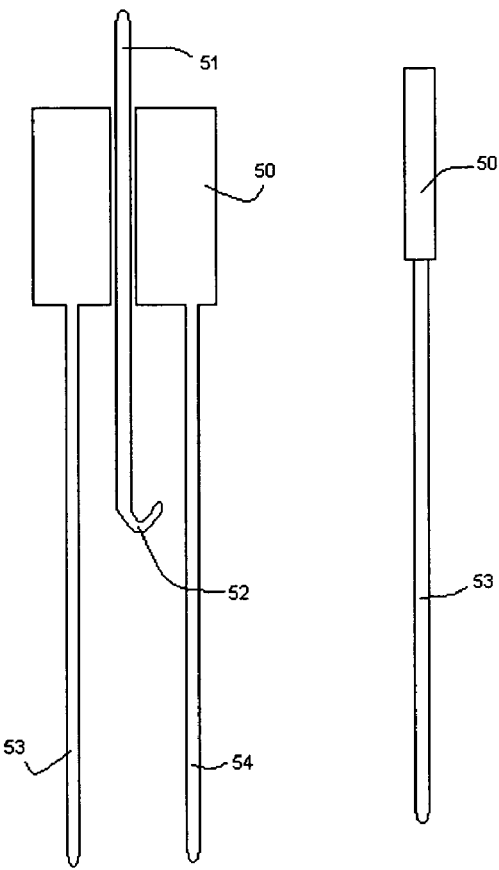
FIG. 27
FIG. 28

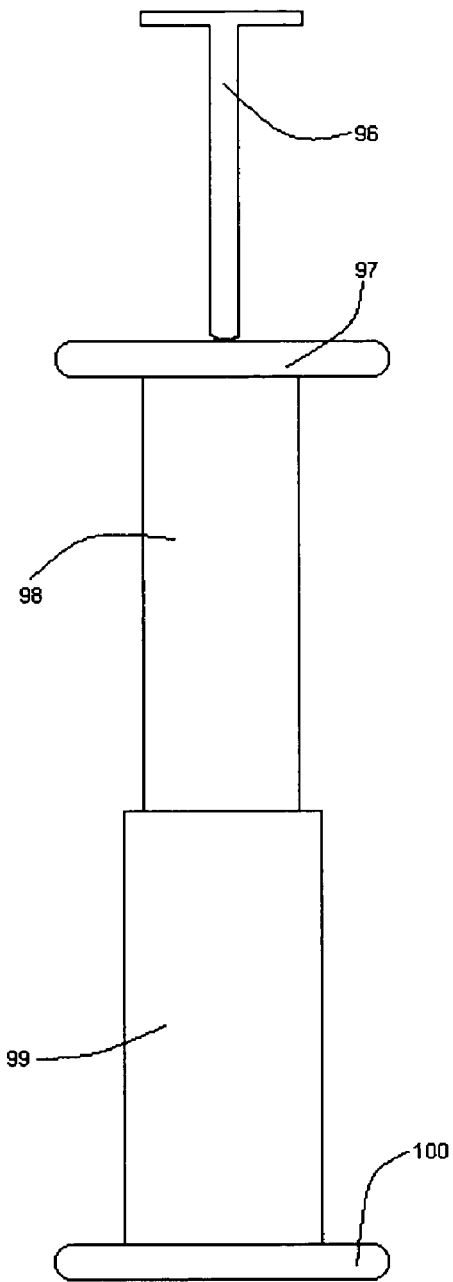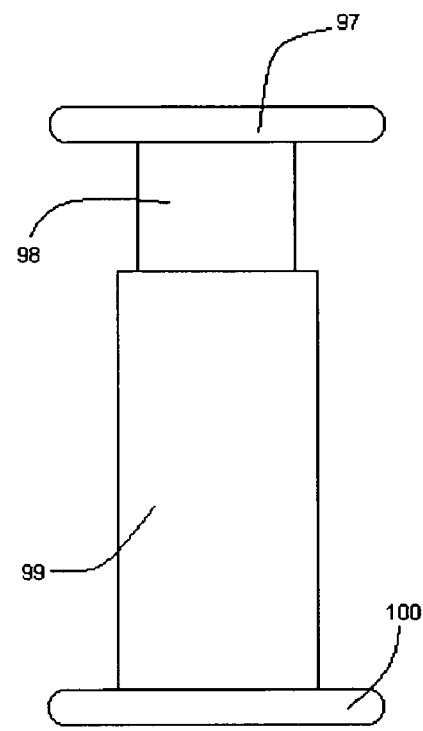
FIG. 52
FIG. 53

CRANIAL FIXATION DEVICE

BACKGROUND OF THE INVENTION

Neurosurgery routinely involves performing craniotomies for exposure of the brain and intracranial contents for various intracranial pathologies including tumors, head injuries, vascular malformations, aneurysms, infections, hemorrhages, strokes, and brain swelling. A craniotomy involves creation of burr holes and removal of a portion of the skull (bone flap) with subsequent approximation of the bone flap for closure. Several methods and fixation devices are available for re-attaching the bone flap to the skull including small metallic or absorbable plates with screws or wires as demonstrated in U.S. Pat. No. 5,578,036 to Stone et al., U.S. Pat. No. 5,916,200 to Eppley et al, and U.S. Pat. No. 5,916,217 to Manthrop et al. Another method has been the use of cranial clamps consisting of two connected circular elements placed on the inside and outside surfaces of the skull.

Cranial clamps are superior to the plates because they are faster to place and do not involve additional drilling of screw holes or downward pressure onto the skull with a screwdriver. Various descriptions of cranial clamps in the art include U.S. Pat. No. 5,707,373 to Sevrain, U.S. Pat. No. 5,800,436 to Lerch, U.S. Pat. No. 6,485,493 to Bremer, U.S. Pat. No. 6,379,363 to Herrington et al., U.S. Pat. No. 6,755,834 to Amis, U.S. Pat. No. 7,048,737 to Wellisz et al., U.S. Pat. No. 7,361,178 to Hearn et al., U.S. Pat. No. 7,387,633 to Ahmad et al., and U.S. Pat. No. 6,685,707 to Roman et al. In U.S. Pat. No. 6,589,244, Sevrain et al. describe a cranial clamp with caps that have studs that lock into a fixed position by screwing into each other.

Unfortunately, placement of these cranial clamps as described in the prior art requires additional devices which further complicates and prolongs the procedure. In general, all of the clamps essentially consist of two circular elements connected by a rod or a shank whereby the circular elements can be moved relative to one another to adjust to the thickness of the bone and fixate the bone flap to the skull. Subsequent to the fixation, the remaining rod is cut off and the clamps are permanently fixed in that position. Their remain several drawbacks to this methodology making the cranial clamps difficult to use and prolong the procedure by requiring an instrument to compress the circular elements together against the bone and once positioned, the need for another instrument for cutting the remaining rod off. Another drawback includes application of excessive force by squeezing the two clamps together against the skull and bone flap. Yet another drawback includes the significant effort required to remove the clamps locked in place in cases of re-operation.

Thus, there is a need for improved cranial fixation devices that allow fast and easier fixation of the bone flap to the skull along with greater ease of removal during a re-operation.

SUMMARY OF THE INVENTION

The present invention relates to a cranial fixation device for fixing a bone flap to the skull. The cranial fixation device includes two heads connected by a spring or an elastic cord allowing for placement without the need for instruments to compress the heads or cut off the excess head connectors. The spring provides an even tension allowing for fixation of the bone flap to the skull without excessive pressure.

In one embodiment of the present invention, the cranial fixation device comprises of two heads connected with a spring inside a telescopic connector. One of the heads is placed on the outer surface of the skull and bone flap and the other on the inner surface of the skull and bone flap. The spring provides a compressive force securing the heads to the skull and bone flap. The telescopic head connector allows the cranial fixation device to be placed in a distracted position until it is implanted to approximate the bone flap to the skull at which time the distracted position is released and the heads compress towards each other. The head placed on the outer skull surface can also contain an opening to accommodate a hook, clamp, or similar instrument to maintain a distracted position prior to implantation. Several locking mechanisms are also described as further illustrated in the detailed description of the preferred embodiments. Essentially, the locking mechanism maintains the heads apart and the telescopic portions in an extended position until ready for implantation to the skull and bone flap. The locking mechanisms can be disengaged either by rotating, pulling, or pushing the heads relative to one another. In another embodiment, one of the telescopic extension walls housing the locking mechanism can be manually compressed thereby disengaging the locking mechanism. The head configuration in the preferred embodiments is circular but could also be rectangular, X-shaped or any other configuration to cover the skull defect. The telescopic configuration in the preferred embodiment is tubular but could also be rectangular. In the preferred embodiment, the telescopic extensions are hollow but in another embodiment one telescopic extension is solid and the other hollow.

In another embodiment, the cranial fixation device comprises of two heads connected with a spring. The head positioned on the outer surface of the skull comprising of an opening which allows placement of an elongated instrument. The configurations of the head opening and elongated instrument provide a distracted position of the two heads with the instrument in place and compression when it is removed. In one embodiment, the head opening is threaded and engages a rod that is partially threaded. The rod and head threads when engaged distract the heads and with rotation of the rod the threads are disengaged allowing compression of the heads thereby also allowing removal of the rod.

Rather than providing a fixed locked position once implanted as described in all the cranial clamps in the prior art, the current invention with the spring or an elastomer band/cord connecting the two heads allow for constrained outward movement of the bone flap relative to the skull in cases of cerebral swelling and subsequently retract the bone flap against the skull once the swelling subsides.

In case there is a need for re-operation, the cranial fixation device can be removed simply with distraction of the heads by pulling them apart either manually or with an instrument. Various embodiments and advantages of the current invention are set forth in the following detailed description and claims which will be readily apparent to one skilled in the art.

BRIEF DESCRIPTION OF THE DRAWINGS

FIG. 6 is a cross-sectional view of another embodiment of the cranial fixation device in an extended state with a collapsible ball locking mechanism.

FIG. 7 is a cross-sectional view of the device in FIG. 6 in a retracted state.

FIG. 26 is a schematic view of another embodiment of the cranial fixation device.

FIG. 27 is a schematic side view of the distracter for the cranial fixation device in FIG. 26.

FIG. 28 is another schematic side view of the distracter in FIG. 27.

FIG. 52 is a schematic view of another embodiment of the cranial fixation device in an extended state.

FIG. 53 is a schematic view of the cranial fixation device in FIG. 52 in a retracted state.

DETAILED DESCRIPTION OF THE PREFERRED EMBODIMENTS

Figure 1:
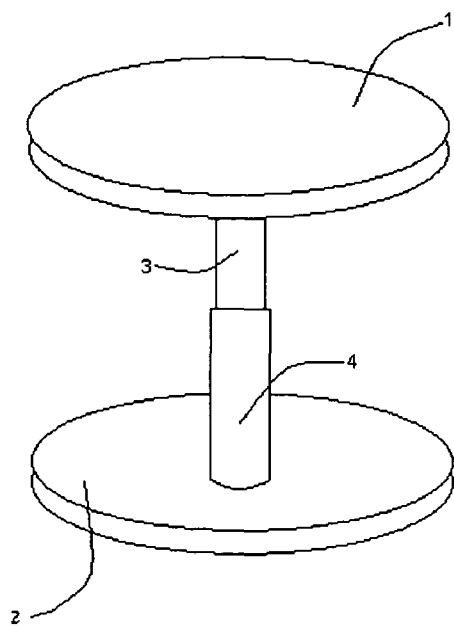
FIG. 1 is a schematic view of one embodiment of the cranial fixation device in an extended state.
Figure 2:
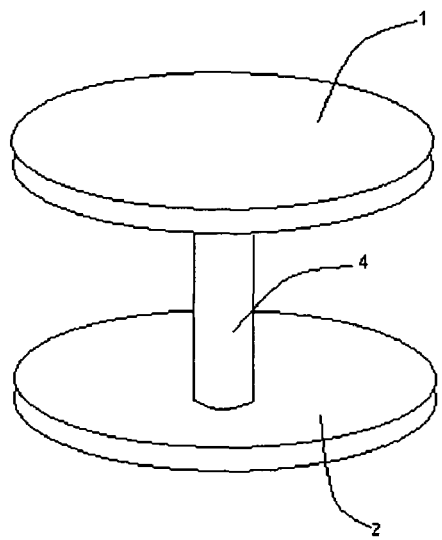
FIG. 2 is a schematic view of the cranial fixation device of FIG. 1 in a retracted state.
Figure 3:
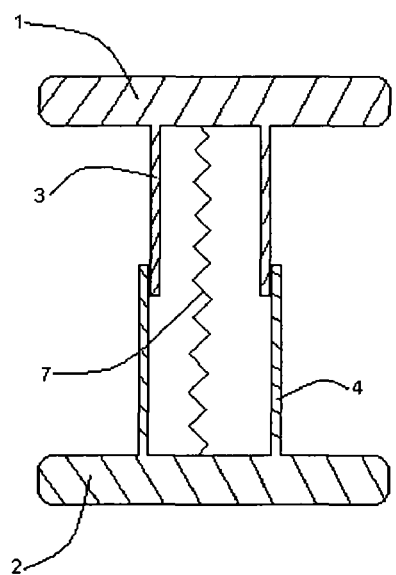
FIG. 3 is a cross-sectional view of the device in FIG. 1.
Figure 4:
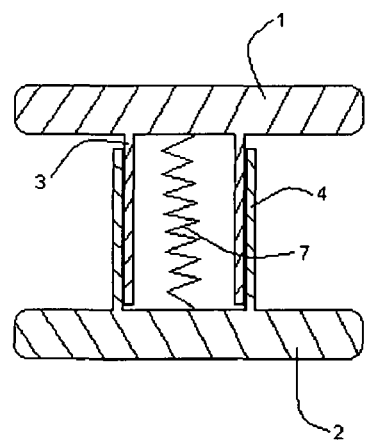
FIG. 4 is a cross-sectional view of the device in FIG. 2
Figure 5:
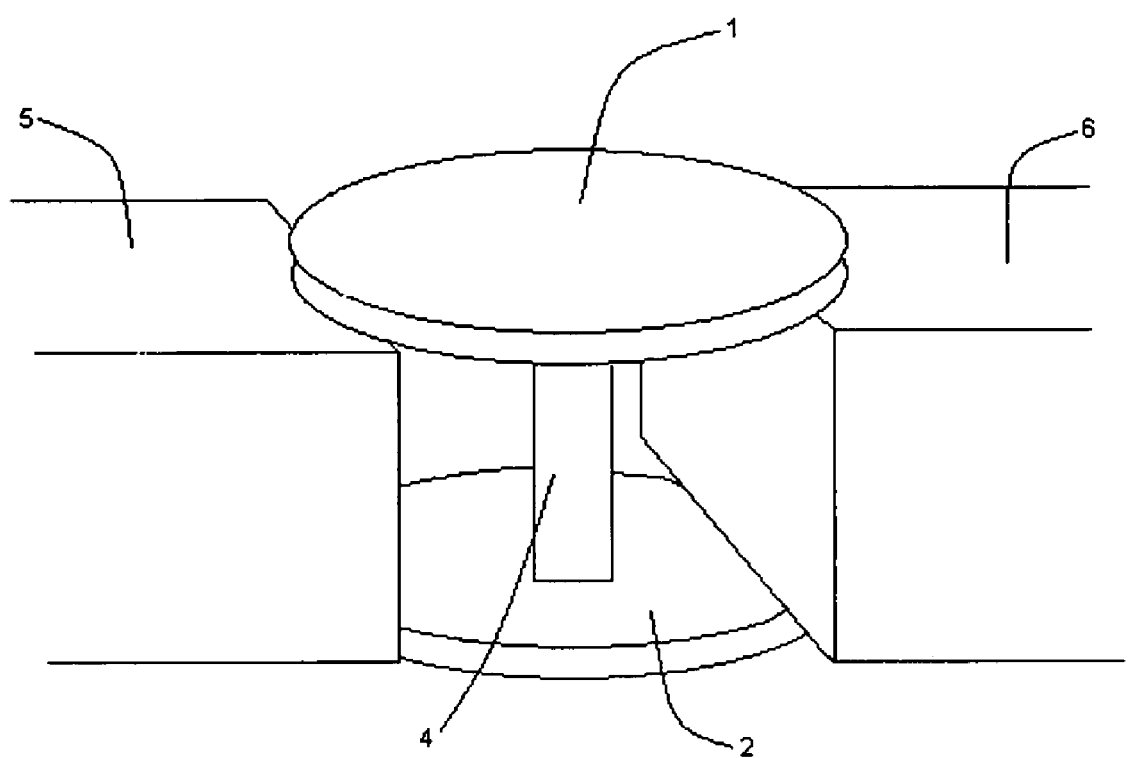
FIG. 5 is a schematic view of the cranial fixation device approximating the bone flap and the skull.

The present invention provides for an easier and faster cranial fixation as well as easy removal in cases of re-operation. The cranial fixation device as shown in FIGS. 1 and 2 comprise of a head 1 with an extension 3 and a head 2 with an extension 4. The extensions 3 and 4 are telescopic and allow for distraction or compression of the heads relative to each other. FIG. 1 shows the telescopic extensions 3 and 4 in a distracted position and FIG. 2 shows the extensions in a compressed position whereby the extension 3 is contained within the extension 4. FIGS. 3 and 4 illustrate the cross sectional longitudinal view of the cranial fixation device. FIG. 3 shows the two heads 1 and 2 along with their telescopic extensions 3 and 4 in a distracted position. The spring 7 is positioned inside the hollow extensions 3 and 4 and connects the two heads 1 and 2. The spring could also be positioned outside the telescopic connectors, which would also provide for a smaller diameter or width of the telescopic extensions. FIG. 4 shows the two heads 1 and 2 along with their telescopic extensions 3 and 4 in a compressed position maintained by the spring 7. FIG. 5 illustrates the cranial fixation device implanted on the skull. The head 1 is positioned on the outer surface of the skull 5 and bone flap 6. The head 2 is positioned on the inner surface of the skull 5 and bone flap 6. The spring inside the telescopic extension 4 allows the two heads to compress against the skull 5 and bone flap 6 thereby approximating them. The cranial fixation device heads are maintained in a distracted position manually and when the manual distraction is released after implantation to the skull the spring compresses the two heads together against the bone flap and skull. An blastomeric band or cord can also be used instead of a spring.

Figure 8:
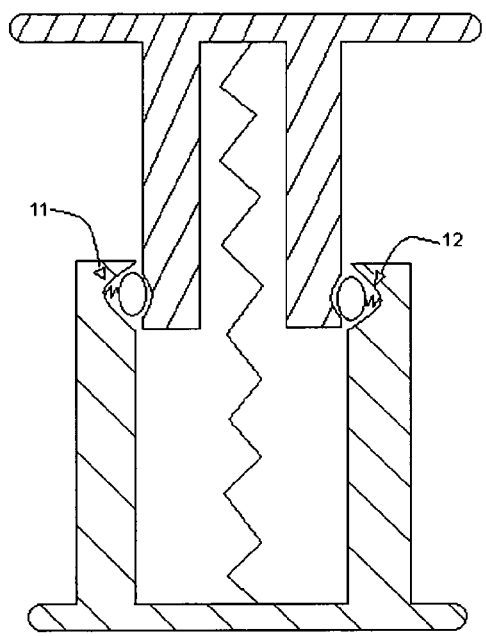
FIG. 8 is a cross-sectional view of another embodiment of the cranial fixation device in an extended state with collapsible ball locking mechanism.
Figure 9:
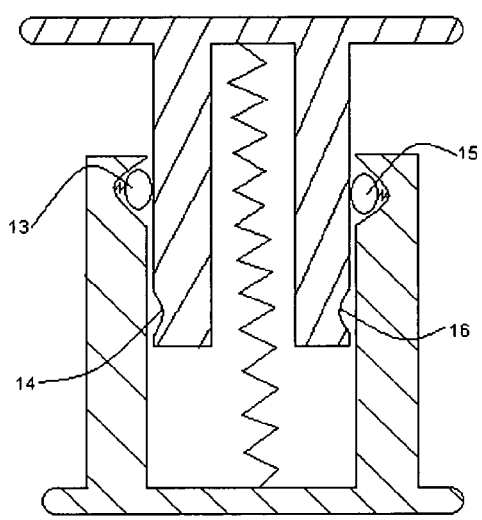
FIG. 9 is a cross-sectional view of another embodiment of the cranial fixation device in a retracted state with a collapsible ball locking mechanism.
Figure 10:
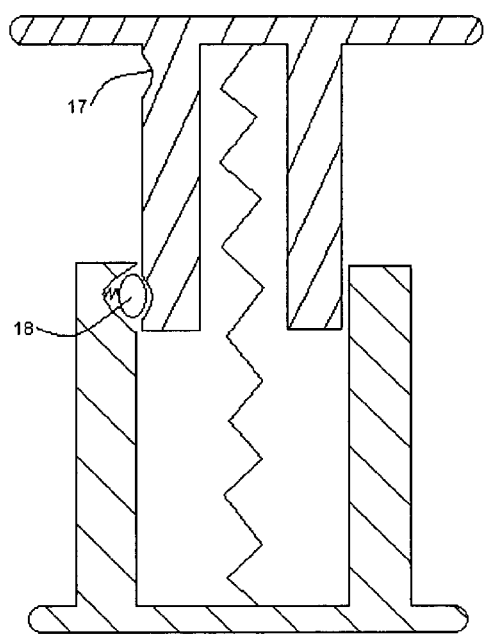
FIG. 10 is a cross-sectional view of another embodiment of the cranial fixation device in an extended state with a collapsible ball locking mechanism.
Figure 11:
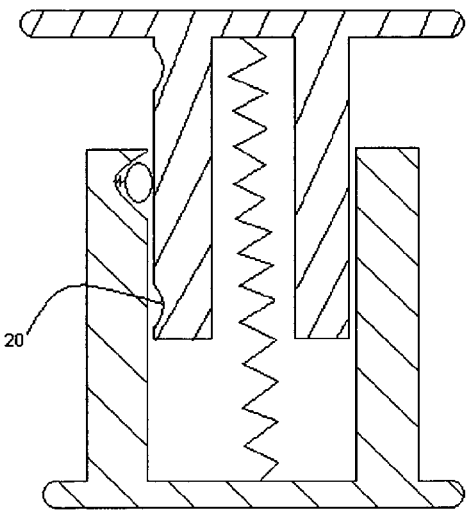
FIG. 11 is a cross-sectional view of another embodiment of the cranial fixation device in a retracted state with a collapsible ball locking mechanism.

In another embodiment, the heads can be maintained in a distracted position by a locking mechanism until ready for implantation. Several locking mechanisms are illustrated in the following embodiments. In one embodiment of the locking mechanism as shown in FIGS. 6 and 7, the telescopic extension 3 of head 1 comprises a socket 8. The telescopic extension 4 of head 2 comprises a collapsible ball 9. The collapsible ball and socket locking mechanism 10 maintains the two heads and their telescopic extensions along with the spring 7 in a distracted position as shown in FIG. 6. The locking mechanism can be released either by rotating the heads relative to one another or slightly distracting or compressing the heads, thereby placing the device in a retracted position as shown in FIG. 7. FIGS. 8-11 illustrate several variations of the ball and socket locking mechanism. FIG. 8 shows circumferential locking mechanisms 11 and 12 engaged in the distracted position and FIG. 9 shows the locking mechanisms disengaged in the retracted position with the collapsible balls 13 and 15 and sockets 14 and 16. FIGS. 10 and 11 illustrate the locking mechanisms which engage during a completely distracted and retracted position. The locking mechanisms comprise of collapsible ball 18 with sockets 17 and 20. In a distracted position the ball 18 engages with the socket 20. In a retracted position the ball 18 engages with the socket 20.

Figure 12:
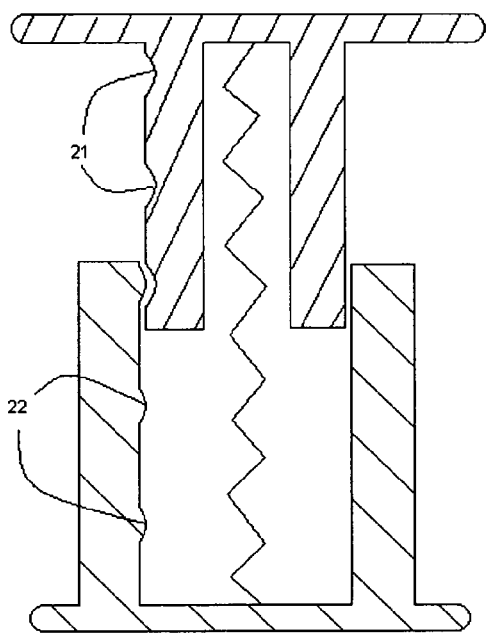
FIG. 12 is a cross-sectional view of another embodiment of the cranial fixation device in an extended state with a ridge and socket locking mechanism.
Figure 13:
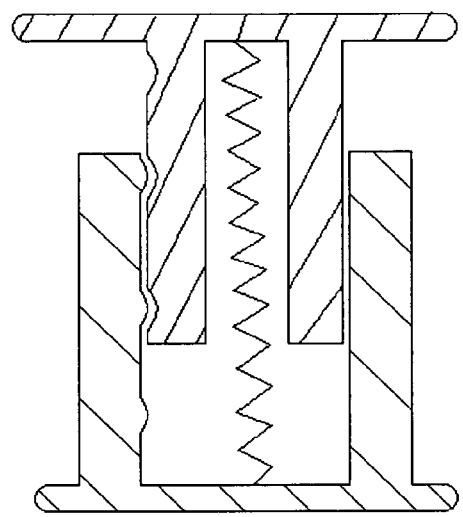
FIG. 13 is a cross-sectional view of another embodiment of the cranial fixation device in a retracted state with a ridge and socket locking mechanism.
Figure 14:
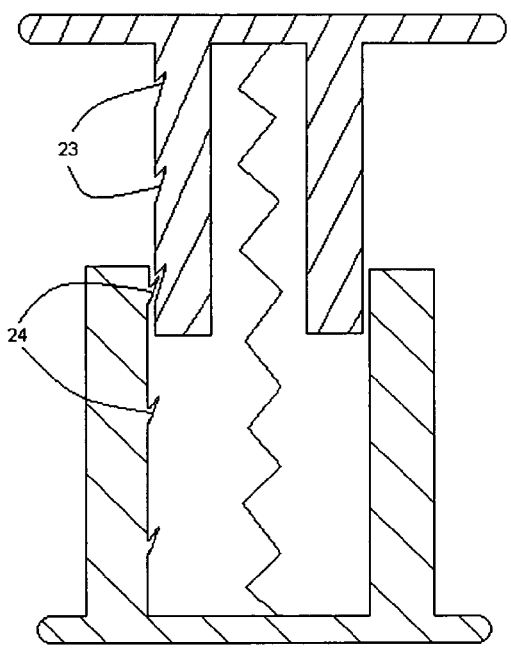
FIG. 14 is a cross-sectional view of another embodiment of the cranial fixation device in an extended state with a ratchet teeth locking mechanism.
Figure 15:
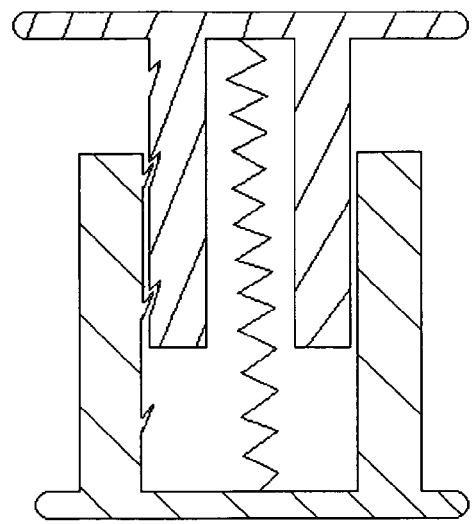
FIG. 15 is a cross-sectional view of another embodiment of the cranial fixation device in a retracted state with a ratchet teeth locking mechanism.
Figure 16:
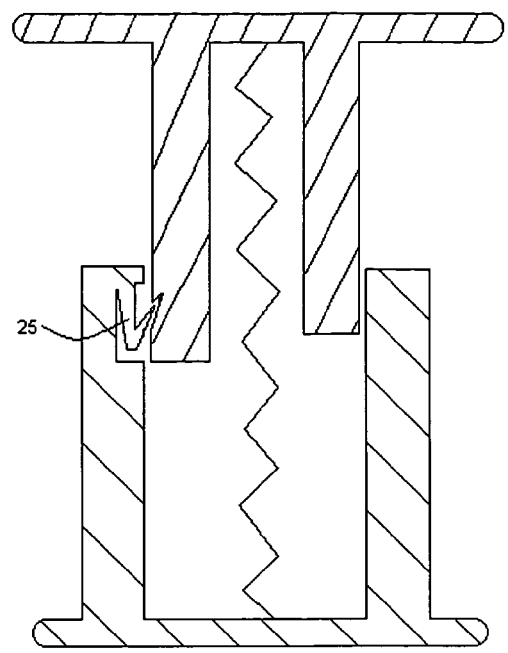
FIG. 16 is a cross-sectional view of another embodiment of the cranial fixation device in an extended state with a collapsible ratchet tooth locking mechanism engaged.
Figure 17:
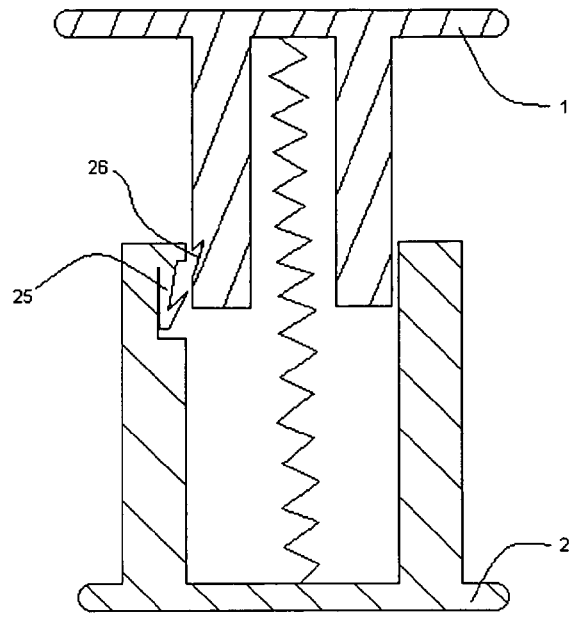
FIG. 17 is a cross-sectional view of the cranial fixation device in FIG. 16 in an extended state with a collapsible ratchet tooth locking mechanism disengaged.
Figure 18:
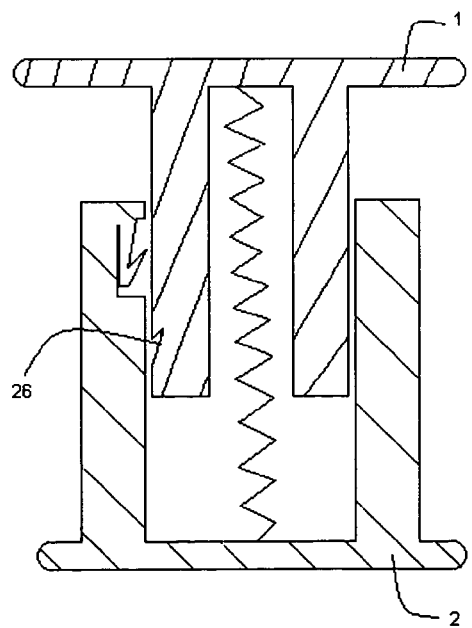
FIG. 18 is a cross-sectional view of the cranial fixation device in FIG. 16 in a retracted state with a collapsible ratchet tooth locking mechanism disengaged.
Figure 19:
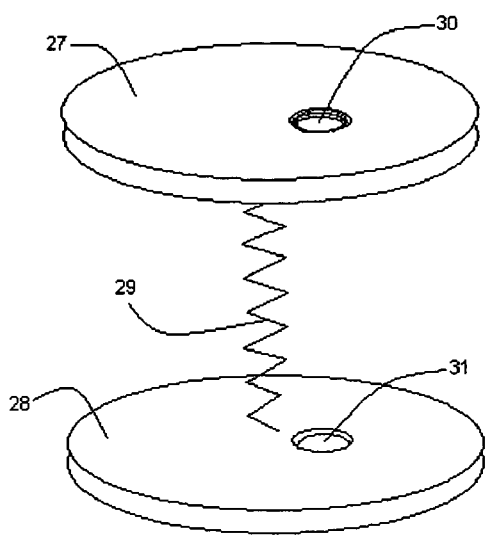
FIG. 19 is a schematic view of another embodiment of the cranial fixation device.
Figure 20:
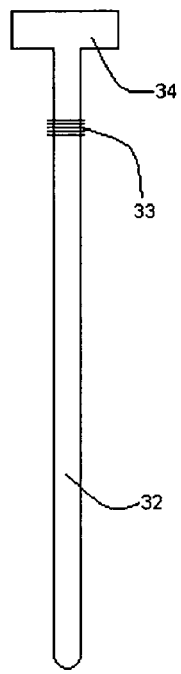
FIG. 20 is a schematic side view of the distracter for the cranial fixation device in FIG. 19.
Figure 21:
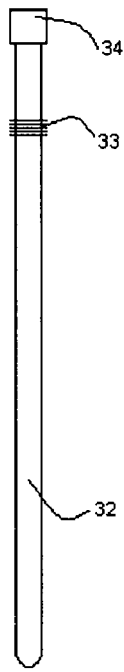
FIG. 21 is another schematic side view of the distracter in FIG. 20.

In another embodiment of the locking mechanism as illustrated in FIGS. 12 and 13 the ridges 22 engage with the grooves 21. In another embodiment, the locking mechanism illustrated in FIGS. 14 and 15 comprises of ratchets 23 and 24. In yet another embodiment, the locking mechanism as shown in FIGS. 16-18 comprises of a collapsible ratchet tooth 25 and corresponding ratchet tooth 26. The two heads and telescopic extensions are maintained in a distracted position when the ratchet teeth 25 and 26 are engaged as shown in FIG. 16. The ratchet tooth 25 collapses and disengages from the ratchet tooth 26 when the two heads 1 and 2 are manually distracted as shown in FIG. 17 thereby allowing for the retraction of the two heads 1 and 2 by the spring as shown in FIG. 18.

Although several locking mechanisms are described in the various embodiments, it is obvious that any variations made to the embodiments by those skilled in the art maintain the broad incentive concepts described herein.

Figure 22:
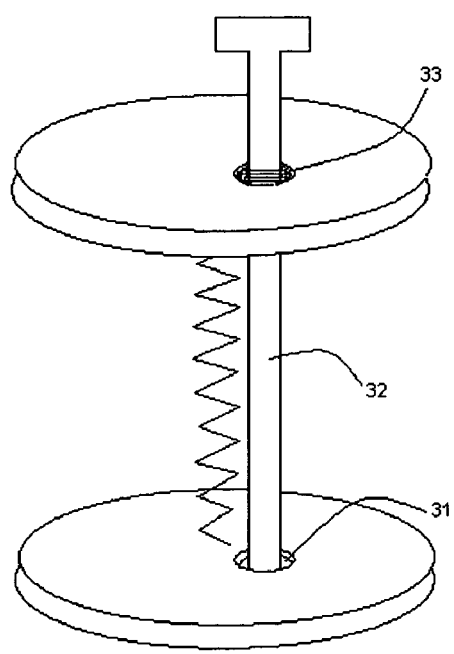
FIG. 22 is a schematic view of the cranial fixation device in FIG. 19 in an extended state with the removable distracter in FIG. 20 in place.
Figure 23:
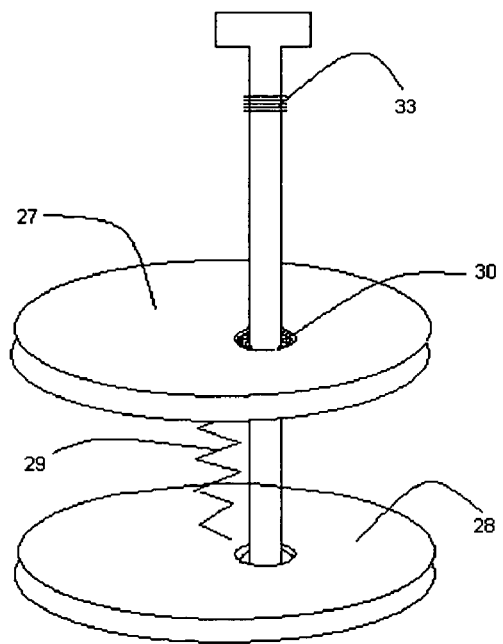
FIG. 23 is a schematic view of the cranial fixation device in FIG. 19 in a retracted state with the distracter in FIG. 20 in place.

In another embodiment of the cranial fixation device as shown in FIGS. 19-23, the first head 27 comprises of a threaded hole 30 and the second head 28 contains a recess 31. The two heads 27 and 28 are connected by a spring 29. The device also comprises of a removable distracter shown in FIGS. 20-21 with a head 34, a shaft 32 with partial threads 33. As shown in FIG. 22 when the distracter is placed through the cranial fixation device with the shaft threads 33 engaged with the head hole threads 30 and the shaft 32 tip resting against the head recess 31, the two heads are in a distracted position ready for implantation onto the skull. As shown in FIG. 23, once the distracter is removed by manual rotation relative to the head 27, the threads 33 on the shaft disengage with the threads 30 in the head 27 and allow for compression between the two heads 27 and 28 by the spring 29.

Figure 24:
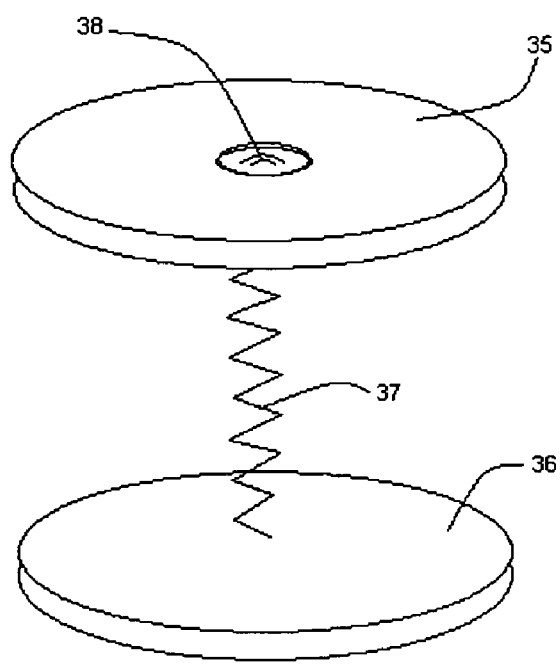
FIG. 24 is a schematic view of another embodiment of the cranial fixation device.
Figure 25:
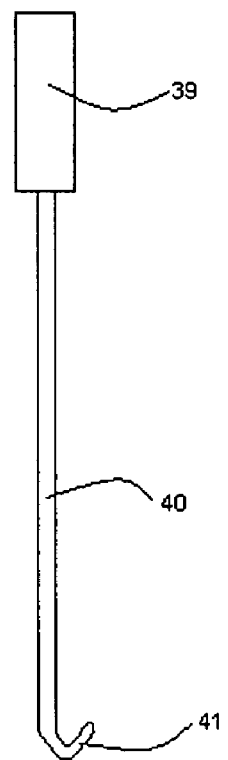
FIG. 25 is schematic view of the distracter for the cranial fixation device in FIG. 24.
Figure 29:
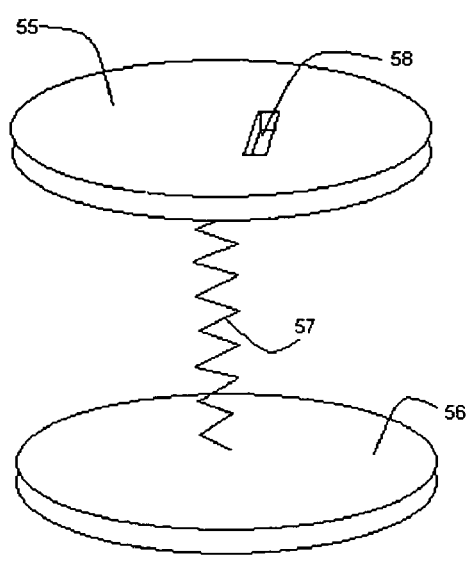
FIG. 29 is a schematic view of another embodiment of the cranial fixation device.
Figure 30:
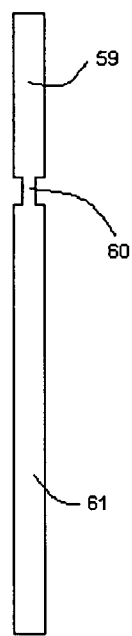
FIG. 30 is a schematic side view of the distracter for the cranial fixation device in FIG. 29.
Figure 31:
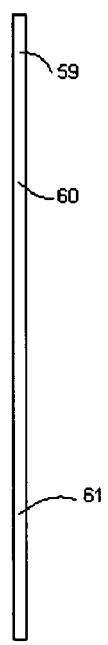
FIG. 31 is another schematic side view of the distracter in FIG. 30.

In another embodiment of the cranial fixation device as shown in FIGS. 24 and 25, the first head 35 is connected to the second head 36 by a spring 37. The first head also comprises of a ridge 38 that can engage a hook instrument. The hook instrument as shown in FIG. 25 contains a head 39, a shaft 40, and a hook 41. The hook 41 engages with the ridge 38 and allows distraction of the plates 35 and 36 relative to each other prior to implantation to the skull.

Figure 32:
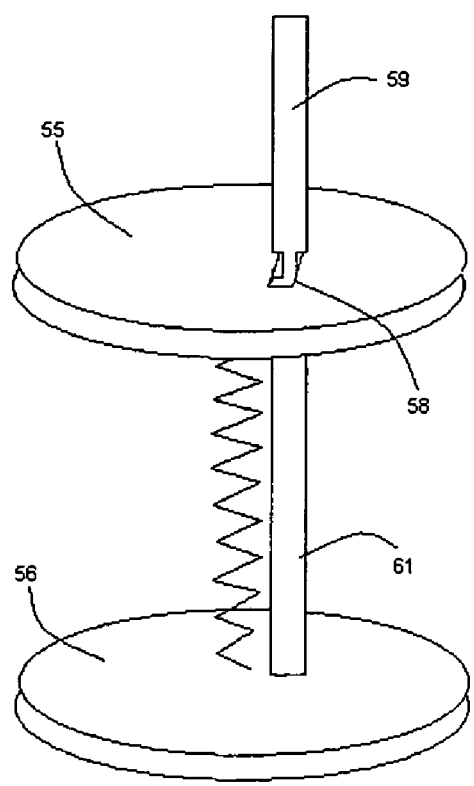
FIG. 32 is a schematic view of the cranial fixation device in FIG. 29 in an extended state with the distracter in FIG. 30 in place.
Figure 33:
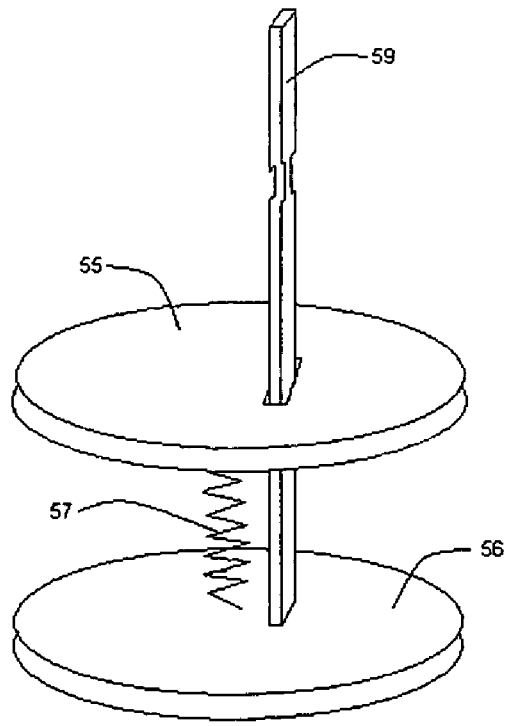
FIG. 33 is a schematic view of the cranial fixation device in FIG. 29 in a retracted state with the removable distracter in FIG. 30 in place.
Figure 34:
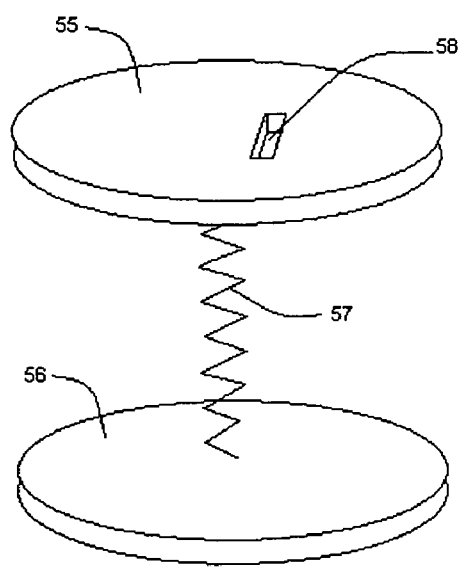
FIG. 34 is a schematic view of another embodiment of the cranial fixation device.
Figure 35:
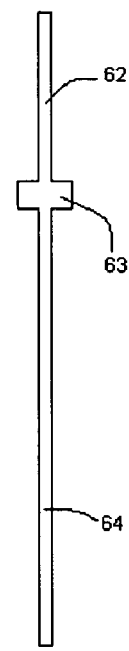
FIG. 35 is a schematic side view of the distracter for the cranial fixation device in FIG. 34.
Figure 36:
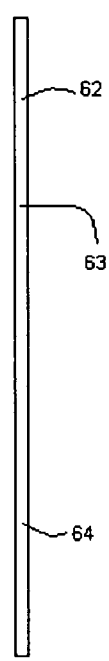
FIG. 36 is another schematic side view of the distracter in FIG. 35.
Figure 37:
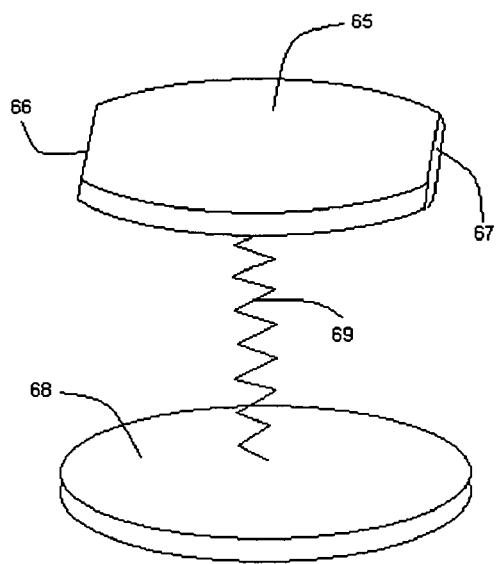
FIG. 37 is a schematic view of another embodiment of the cranial fixation device.
Figure 38:
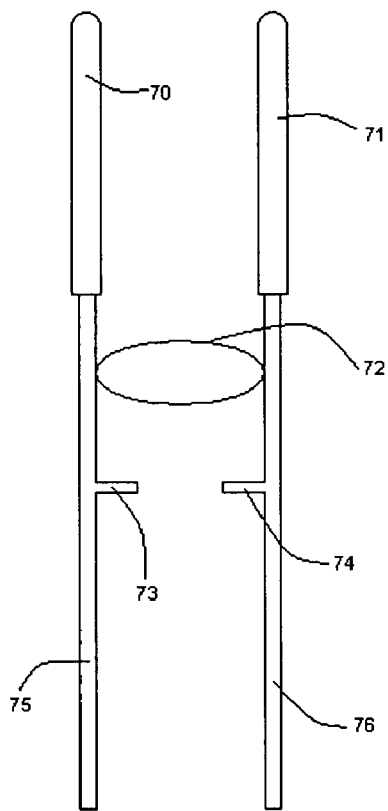
FIG. 38 is a schematic side view of the distracter for the cranial fixation device in FIG. 37.

In another embodiment of the cranial fixation device as shown in FIGS. 26-28, the first head 42 comprises of a ridge 45 and holes 46 and 47. The second head 43 comprises of two recesses 48 and 49. A spring 44 connects the two heads and maintains the two heads compressed unless placed in a distracted position by a distracter illustrated in FIGS. 27 and 28. The distracter comprises of a head 50 with two pins 53 and 54. The head 50 also contains an opening for a hook 52 with a hook shaft 51. The distracter pins 53 and 54 when positioned through the head holes 46 and 47 with the tips resting on the head recesses 48 and 49 provide counter-traction and enable the hook 52 to engage with the ridge 45 and provide traction. The traction and counter-traction provided by the distracter thereby distract the two heads 42 and 43 before implantation and once the heads are positioned on the outside and inside surface of the skull and bone flap the hook is disengaged from the ridge and allows the spring to compress the two heads and secure the bone flap to the skull. In another embodiment of the cranial fixation device as shown in FIGS. 29-33, the first head 55 comprises of a rectangular opening 58. The head 55 is connected to the second head 56 by a spring 57. The spring maintains the two heads in a compressed position. The distracter shown in FIGS. 30 and 31 comprises of a head 59, shaft 61, and a narrow rectangular portion 60. The rectangular opening 58 in the first head 55 is configured to allow placement of the distracter and once the narrow portion 60 of the distracter is positioned in the opening 58, rotation of the distracter by 90 degrees engages the first head. As shown in FIG. 32, the two heads 55 and 56 are maintained in a distracted position by the distracter 59 placed through the head opening 58. The rectangular narrowing 60 in the shaft rests against the inner surface of the first head 55 with the shaft tip 61 resting on the inner surface of the second head 56. As illustrated in FIG. 33, the two heads 55 and 56 are allowed to compress by the spring 57 once the distracter 59 is rotated 90 degrees allowing for disengagement of the distracted position of the two heads and removal of the distracter. In another embodiment of the distracter as shown in FIGS. 34-36, the distracter comprises of a head 62, shaft 64, and a wider rectangular portion 63. The rectangular opening 58 in the first head 55 is configured to allow placement of the distracter and once the wider portion 63 is passed through the opening, the distracter shaft is rotated 90 degrees allowing for the wider portion 63 to rest against the inner surface of the head 55 and maintaining a distracted position of the two heads. Similarly the distracted position can be released by rotating the distracter to 90 degrees again whereby allowing the two heads to compress and secure the bone flap to the skull.

Figure 39:
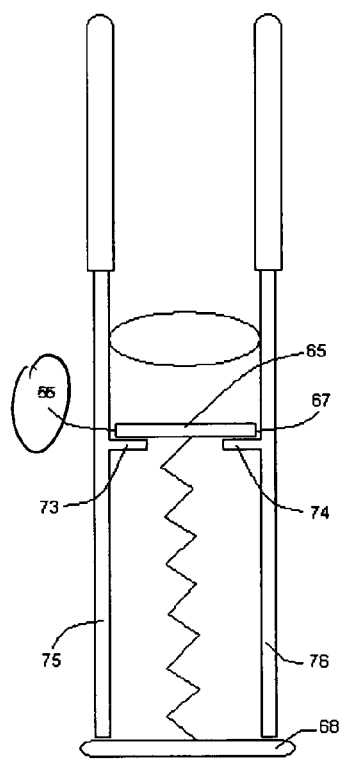
FIG. 39 is a side view of the cranial fixation device in FIG. 36 in an extended state with the distracter in FIG. 38 in place.
Figure 40:
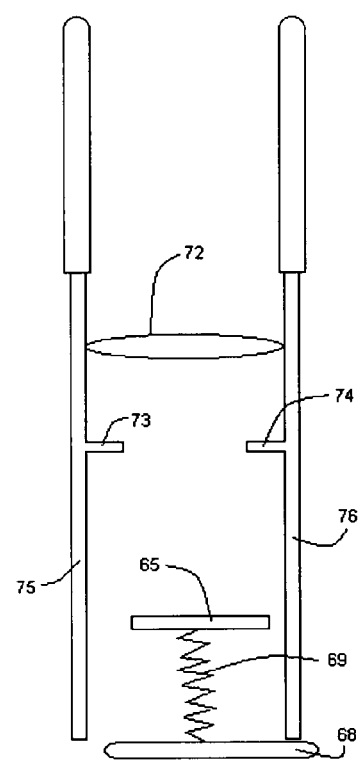
FIG. 40 is a side view of the cranial fixation device in FIG. 36 in a retracted state with the distracter in FIG. 38 disengaged.
Figure 41:
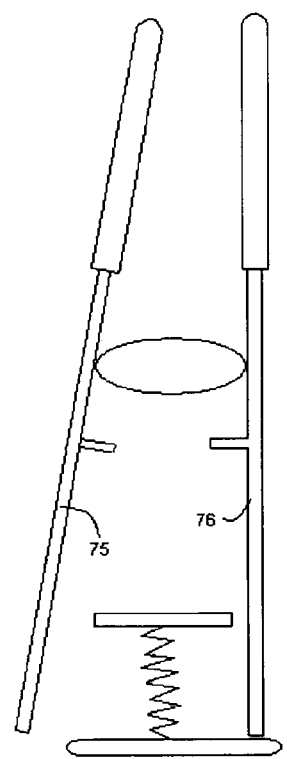
FIG. 41 is a side view of the cranial fixation device in FIG. 36 with another embodiment of the distracter.

In another embodiment, the cranial fixation device as illustrated in FIGS. 37-41 comprises of the first head 65, the second head 68, and a spring 69. The first head 65 has two cut off edges 66 and 67. The distracter shown in FIG. 38 comprises of two heads 70 and 71, two shafts 75 and 76, ridges 73 and 74, and a connector 72. FIG. 39 shows the distracter in place with the cranial fixation device in the distracted position. The inner surface of the head 65 and the edges 66 and 67 rest upon the distracter shaft ridges 73 and 74. The distracter shaft tips 75 and 76 rest on the inner surface of the head 68. FIG. 40 shows the distracter connector 72 spreading the two distracter shafts 75 and 76 apart, thereby disengaging the head 65 resting upon the shaft ridges 73 and 74 which allows the spring 69 to compress the two heads 65 and 68 together. In other embodiment of the distracter, the two shafts 75 and 76 can tilt either inwards or outwards to disengage the cranial fixation device as shown in FIG. 41.

Figure 42:
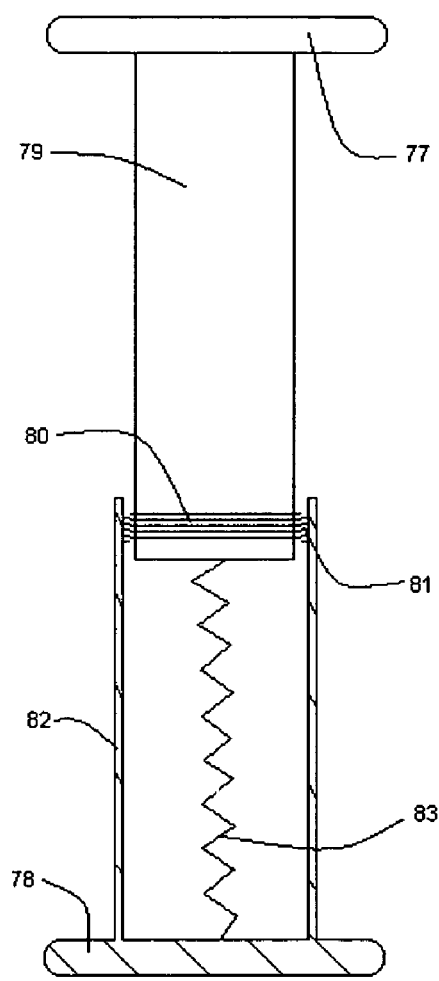
FIG. 42 is a partially schematic and cross-sectional view of another embodiment of the cranial fixation device in an extended state.
Figure 43:
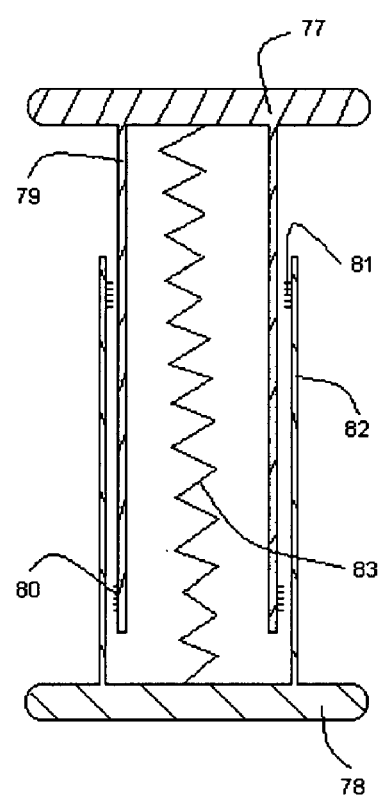
FIG. 43 is a cross-sectional view of the cranial fixation device in FIG. 42 in a retracted state.
Figure 44:
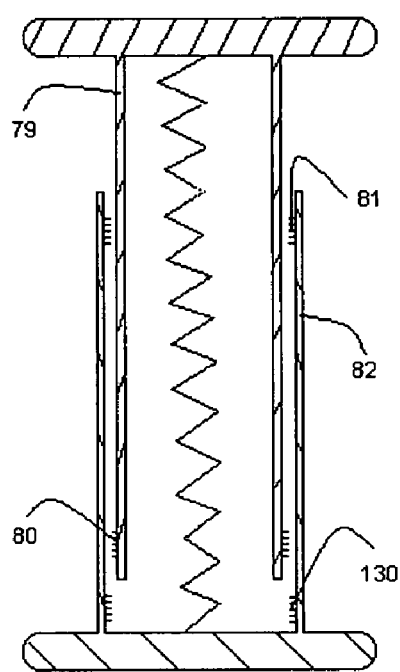
FIG. 44 is a cross-sectional view of another embodiment of the cranial fixation device in a retracted state.
Figure 45:
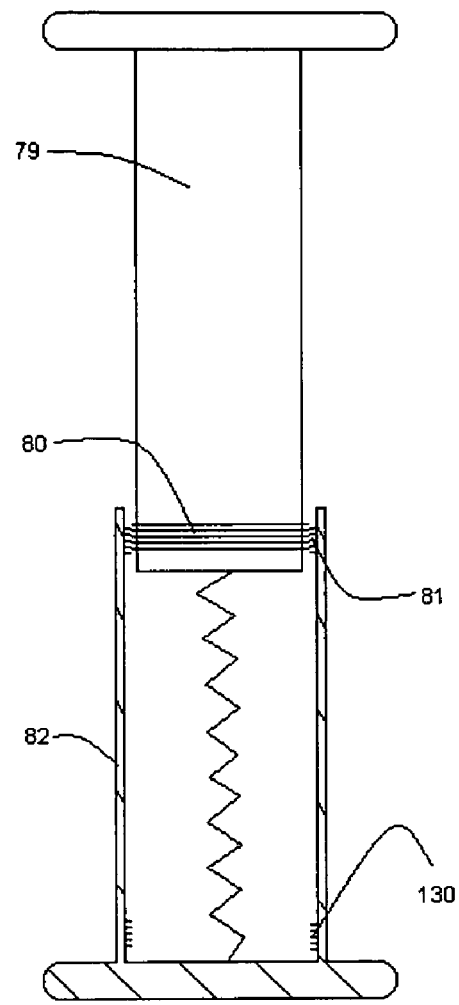
FIG. 45 is a partially schematic and cross-sectional view of the cranial fixation device in FIG. 44 in an extended state.

In another embodiment, the cranial fixation device illustrated in FIGS. 42-44 comprises of a first head 77 with a telescopic extension 79 and a second head 78 with a telescopic extension 82. The telescopic extensions are hollow cylinders and contain a spring 83 connecting the two heads 77 and 78. The outer portion of the first telescopic portion distal end 80 and the inner portion of the second telescopic distal end 81 are threaded. As shown in FIG. 42 the cranial fixation is in an extended position with the telescopic extension threads 80 and 81 engaged. Once the device is placed through the burr hole opening between the skull and the bone flap, the head 77 is rotated relative to the head 78 until the threads disengage thereby allowing the spring to compress the heads together against the skull and bone flap. The compressed state of the heads is illustrated in FIG. 43. The head 77 with the telescopic extension 79 slides inside the telescopic extension 82 of the head 78, facilitated by the spring 83. The partial threads 80 and 81 are in the disengaged position. In another embodiment as shown in FIGS. 44 and 45, the inner portion of the second telescopic extension 82 comprises of partial threads at the proximal end 130 and distal end 81. Once the heads are in a contracted position, they can also be locked by the proximal threads 130 on extension 82 engaging with the distal threads 80 on extension 79.

Figure 46:
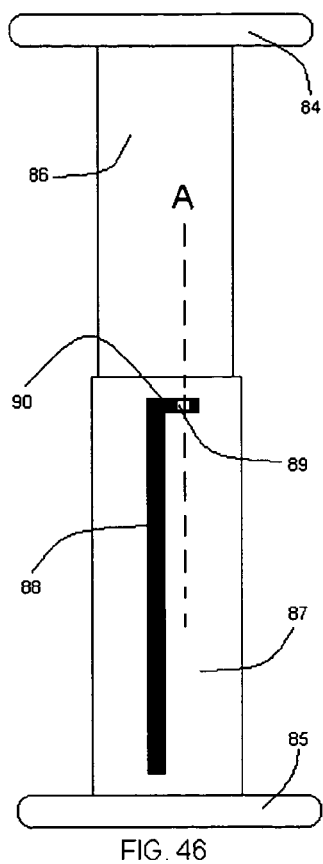
FIG. 46 is a schematic view of another embodiment of the cranial fixation device in an extended state.
Figure 47:
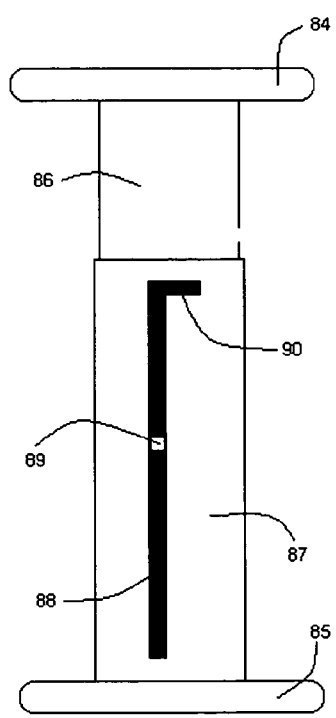
FIG. 47 is a schematic view of the cranial fixation device in FIG. 46 in a retracted state.
Figure 48:
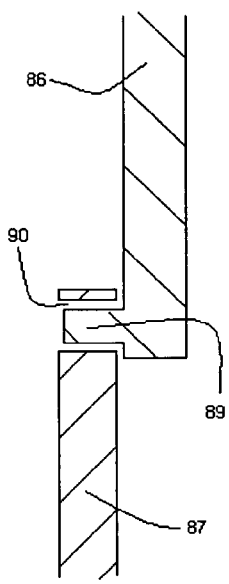
FIG. 48 is an enlarged cross-sectional view of the cranial fixation device taken along line A in FIG. 46.

In another embodiment the cranial fixation device illustrated in FIGS. 46-48 comprises of a head 84 with a cylindrical extension 86 slidably coupled to a hollow cylindrical extension 87 with a head 85. The two heads are connected by a spring inside the telescopic extensions. As shown in FIG. 46 the two heads are maintained in a distracted position by a locking mechanism comprised of a ridge 89 at the distal end of the telescopic extension 86 and a longitudinal opening 88 in the telescopic extension 87. The longitudinal opening is L-shaped and when the ridge is engaged in the short arm 90 of the L-shape, the heads are in a distracted position. As shown in FIG. 47 rotating the heads 84 and 85 relative to each other places the ridge 89 in the long arm of the L-shaped opening 88, thereby, allowing the heads to compress and the telescopic extensions to slide into each other. FIG. 48 is a magnified view of the locking mechanism along the line A with the ridge 89 on the telescope 86 engaging the corresponding opening 90 in the telescope 87.

Figure 49:
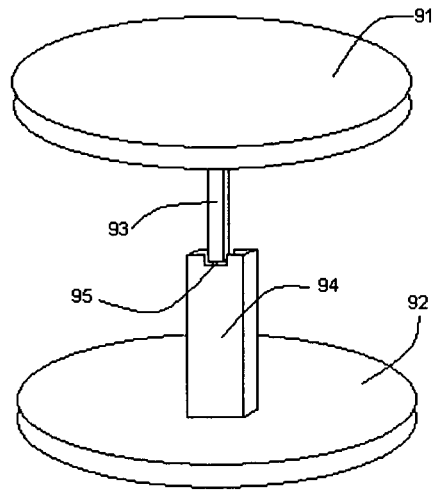
FIG. 49 is a schematic view of another embodiment of the cranial fixation device in a locked and extended position.
Figure 50A:
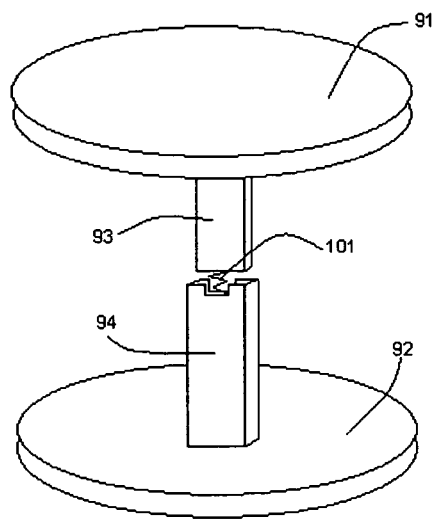
FIG. 50A is a schematic view of the cranial fixation device in FIG. 49 in an unlocked and extended position.
Figure 50B:
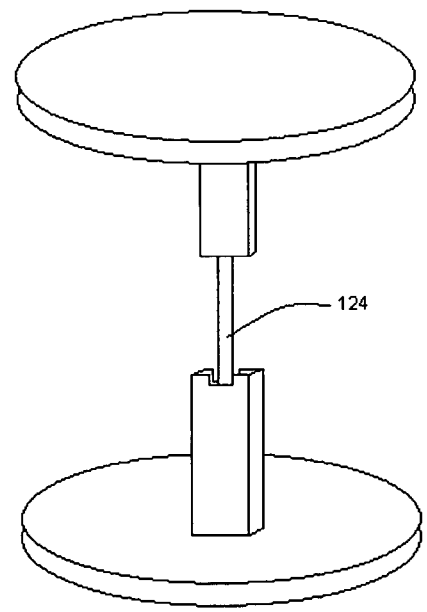
FIG. 50B is a schematic view of another embodiment of the cranial fixation device in FIG. 49 in an unlocked and extended position.
Figure 51:
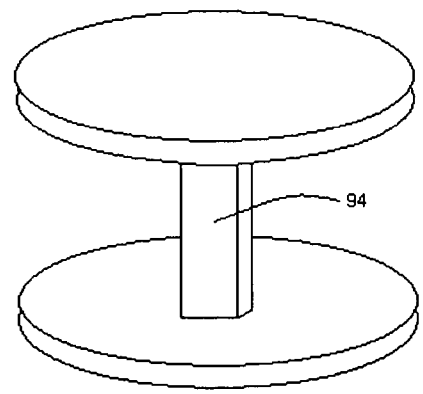
FIG. 51 is a schematic view of the cranial fixation device in FIG. 49 in a retracted position.

In another embodiment illustrated in FIGS. 49-51 the cranial fixation device comprises of a head 91 with a rectangular telescopic extension 93 slidably coupled to a hollow rectangular telescopic extension 94 with a head 92. The telescopic extension 94 has a recess 95 at the distal end. As shown in FIG. 49 when the telescopic extension 93 is rotated 90 degrees in an extended state relative to the telescopic extension 94, the distal end of the telescopic extension 93 rests in recess 95 at the distal end of the telescopic extension 94. As shown in FIG. 50A rotation of the head 91 against head 92 another 90 degrees places the corresponding telescopic extensions parallel to each other. The spring 101 subsequently retracts the extension 93 into the extension 94. FIG. 50B illustrates the fixation device with the elastic band 124 inside the telescopic extensions instead of the spring. As shown in FIG. 51 the telescopic extension 93 placed in a parallel position slides into the telescopic extension 94 thereby placing the device in a retracted state.

The telescopic engaging mechanism can be released either by rotating the heads relative to one another or slightly distracting the heads further. In any of the above described embodiments, the head placed on the outer skull surface can also contain an opening to accommodate a hook or similar instrument to maintain a distracted position. The hook can also be used to rotate or further distract the head in the embodiments that contain a locking mechanism. The head on the outer portion of the skull can also contain an extension as illustrated in FIG. 52. The head 97 positioned on the outer surface of the skull comprises of an extension 96 and a telescope 98. The head 100 positioned on the inner surface of the skull comprises of a telescope 99. The extension 96 is used to distract or rotate head 97 against head 100. The extension 96 can be removed by manually snapping it off or with the use of a cutting instrument. FIG. 53 illustrates the cranial fixation device with the telescopic extensions 98 and 99 in a retracted position with the extension 96 removed from the head 97.

Figure 54:
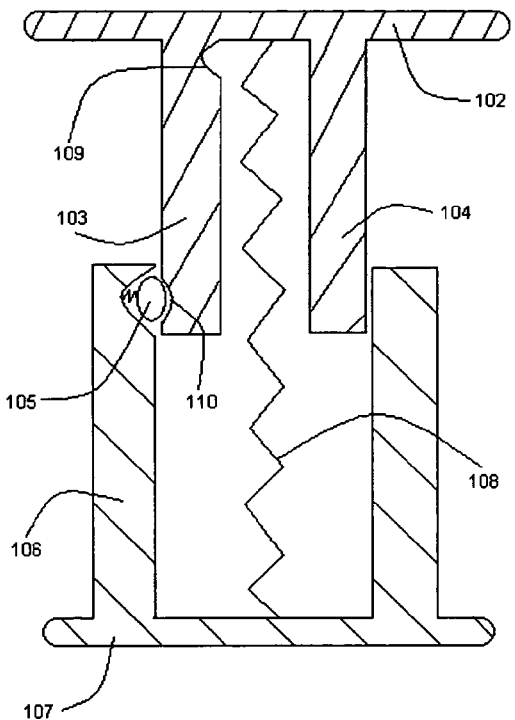
FIG. 54 is a cross-sectional view of another embodiment of the cranial fixation device in a locked and extended position.
Figure 55:
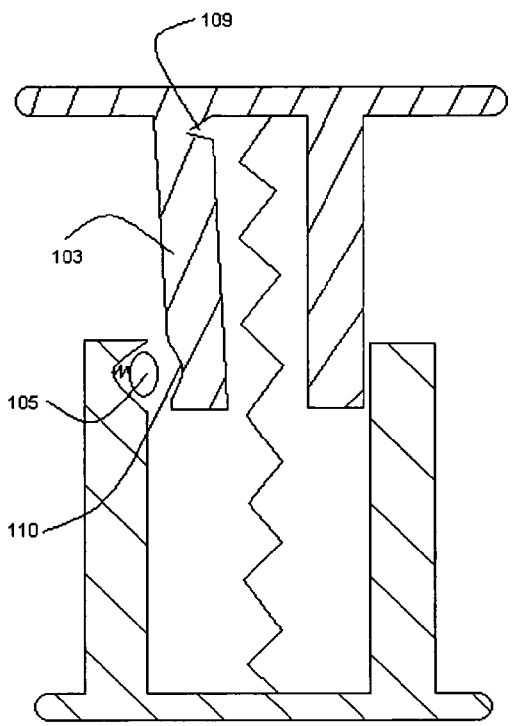
FIG. 55 is a cross sectional view of the cranial fixation device in FIG. 54 in an unlocked extended position.
Figure 56:
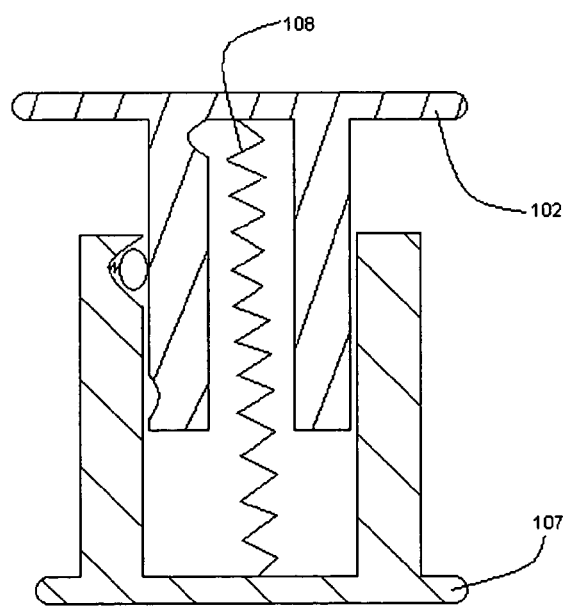
FIG. 56 is a cross sectional view of the cranial fixation device in FIG. 54 in an unlocked retracted position.
Figure 57:
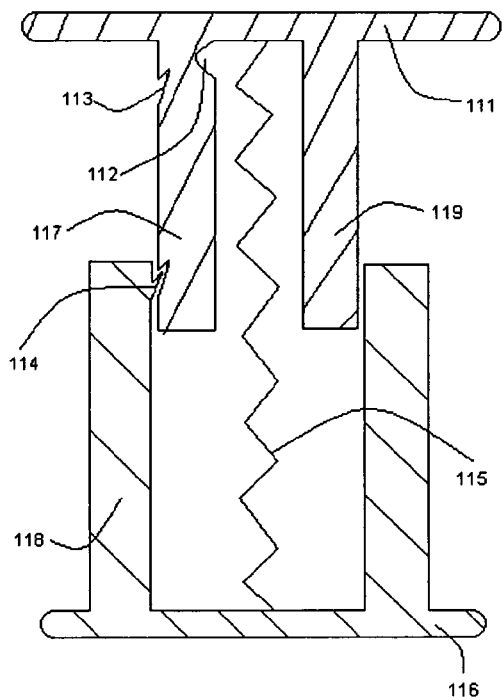
FIG. 57 is a cross-sectional view of another embodiment of the cranial fixation device in a locked and extended position.
Figure 58:
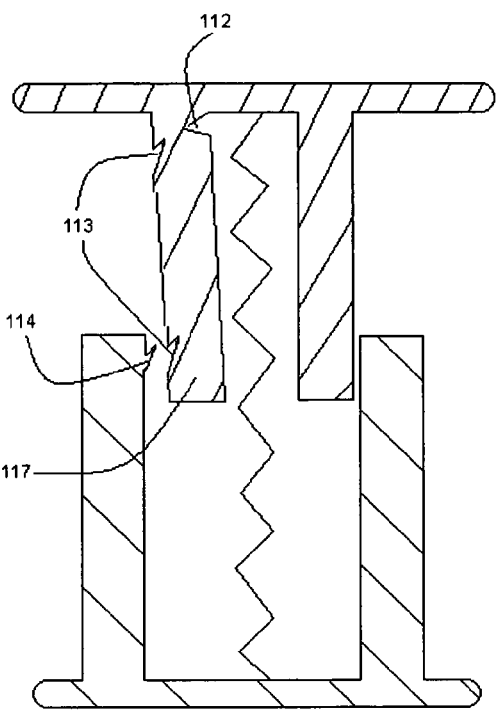
FIG. 58 is a cross sectional view of the cranial fixation device in FIG. 57 in an unlocked extended position.
Figure 59:
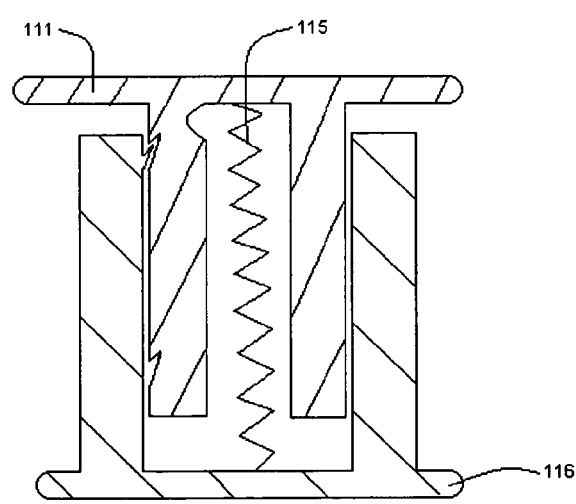
FIG. 59 is a cross sectional view of the cranial fixation device in FIG. 57 in an unlocked retracted position.
Figure 60:
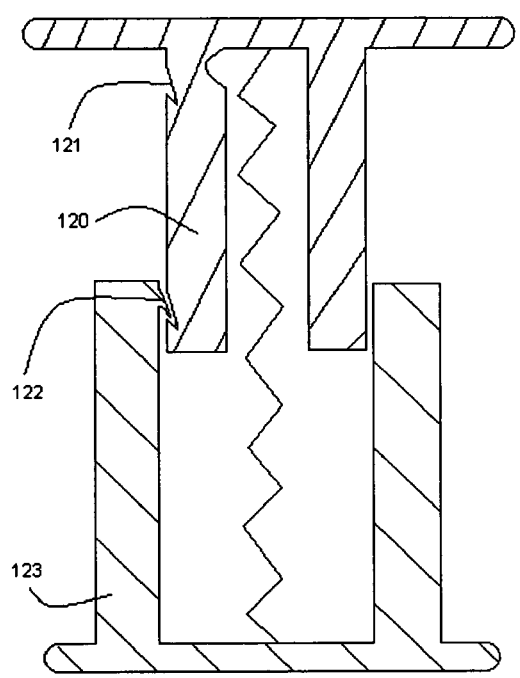
FIG. 60 is a cross-sectional view of another embodiment of the cranial fixation device in a locked and extended position.
Figure 61:
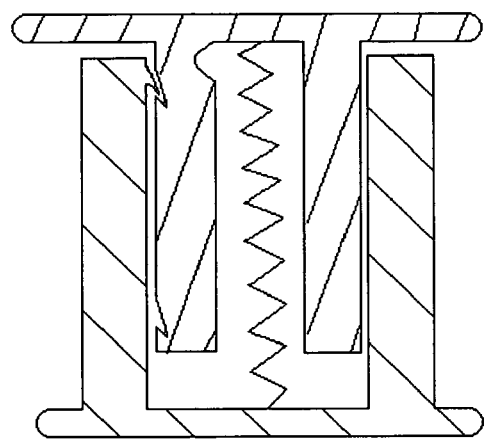
FIG. 61 is a cross sectional view of the cranial fixation device in FIG. 60 in an unlocked retracted position.

In another embodiment as illustrated in FIGS. 54-56, the cranial fixation device has a head 102 with two walls 103 and 104 and a head 107 with a rectangular wall 106. The locking mechanism is a ball 105 and socket 110 engaged in an extended position of the heads as shown in FIG. 54. The wall 103 also contains a recess 109 which allows it to flex inward with manual compression as illustrated in FIG. 55, thereby disengaging the locking mechanism by moving the socket 110 away from the ball 105. As shown in FIG. 56, once the locking mechanism is disengaged, the spring 108 retracts the two heads 102 and 107 towards each other. In another embodiment the wall 106 can also be tubular. In another embodiment as illustrated in FIGS. 57-59, the cranial fixation device has a head 111 with two walls 117 and 119 and a head 116 with a rectangular or tubular wall 118. The locking mechanism is a ratchet tooth pointing upwards 114 and recess 113 engaged in an extended position of the heads as shown in FIG. 57. The wall 117 also contains a recess 112 which allows it to flex inward with manual compression as illustrated in FIG. 58, thereby disengaging the locking mechanism by moving the ratchet tooth 114 away from the recess 113. As shown in FIG. 59, once the locking mechanism is disengaged, the spring 115 retracts the two heads 111 and 116 towards each other. FIGS. 60 & 61 illustrate the ratchet teeth 122 pointing downwards along with the recess 121 on the flexible wall 120 with an extended position of the device in FIG. 60 and a retracted position in FIG. 61.

Figure 62:
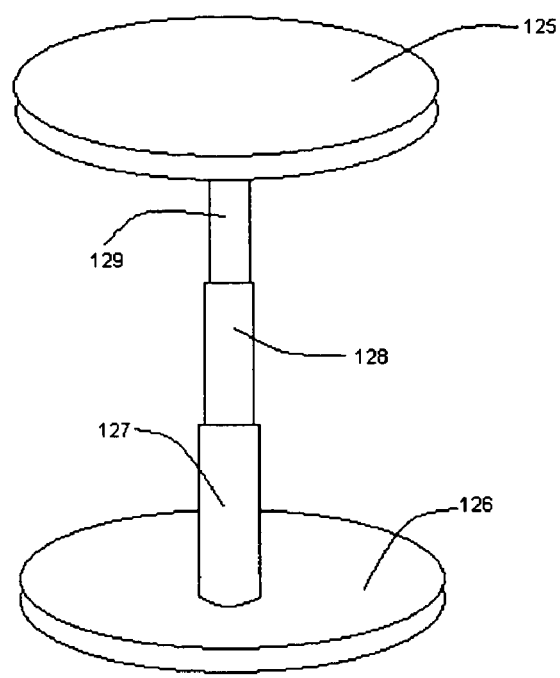
FIG. 62 is a schematic view of another embodiment of the cranial fixation device in an extended position.
Figure 63:
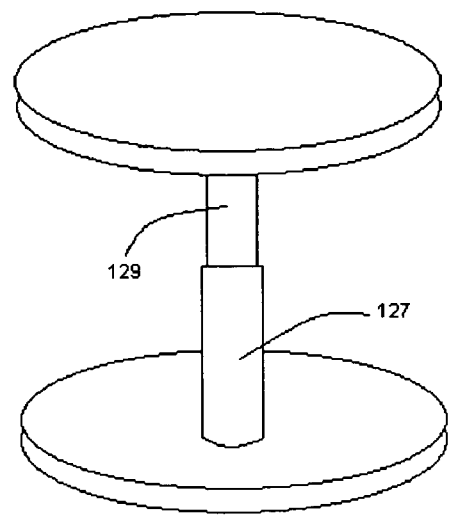
FIG. 63 is a schematic view of the cranial fixation device in FIG. 62 in a partially extended position.
Figure 64:
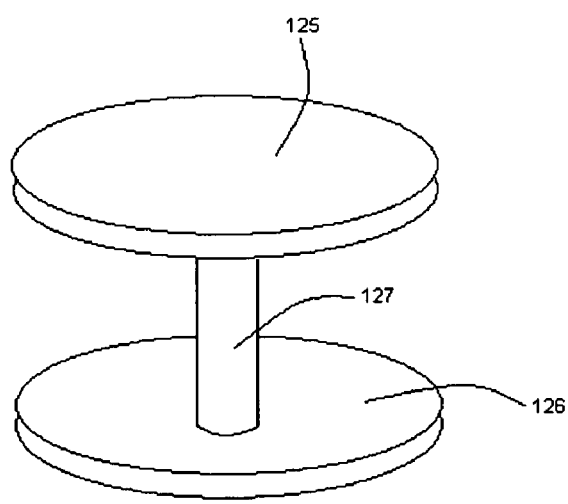
FIG. 64 is a schematic view of the cranial fixation device in FIG. 62 in a completely retracted position.

In another embodiment, the locking mechanisms described above can engage during a distracted position as well as a retracted position. While the spring connecting the two heads illustrated in the various embodiments above resides inside the telescopic component, it can be placed outside the telescopic portions. In other embodiments the telescopic extensions can be positioned inside the central hollow portion of the spring. The telescopic extensions from each head can also be connected with another intermediary telescopic component to allow further distraction of the heads if needed and retract into each other. As illustrated in FIGS. 62-64, another embodiment the cranial fixation device comprises a head 125 with an extension 129 and a head 126 with a hollow extension 127. The extensions 127 and 129 are telescopically connected by an intermediary hollow extension 128. The two heads 125 and 126 are connected by a spring or an elastic band either inside or outside the telescopic extensions. FIG. 62 illustrates the device in a distracted position with telescopic extensions 127, 128, and 129. FIG. 63 illustrates the device in a partially distracted position with the telescopic extensions 127 and 129. The intermediate extension 128 has telescoped inside the extension 127. FIG. 64 illustrates the device in a completely retracted position with the intermediate extension 128 and head extension 129 telescoped inside extension 127, thereby compressing the heads 125 and 126 closer together.

Although the flexible component connecting the two heads described in the various embodiments of the cranial fixation device is a spring, it can also be an elastomeric band or cord. The elastomer can be made out of rubber, rubber derivative, silicone or any elastic biocompatible material. It could also be made out of a shape memory alloy like nitinol. In the various embodiments described herein the preferred head configuration is circular so as to cover the burr hole or skull opening. Other head configurations could be rectangular, square, X-shaped, fan shaped, or any other configuration able to connect the skull to the bone flap. Similarly, the telescopic configurations described are either cylindrical or rectangular and hollow designed to fit into the burr hole or skull opening. Other telescopic configurations could be partially solid, tapered, V-shaped or any other configuration that fit's the skull opening. The cranial fixation device can be made of titanium or titanium alloy for MRI imaging compatibility. It could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of ϵ-caprolactone, trimethylene carbonate, and para-dioxanone), or allograft or xenograft bone that is absorbed by the body over time once the bone flap has fused with the skull. Alternatively, it could be made of a radiolucent material (polyetheretherketone), plastic, or a combination of plastic and metal to reduce CT and MRI imaging artifact. Although the application for the cranial fixation device described in the various embodiments is for fixation of the bone flap to the skull following a craniotomy, it can also be used to cover a burr hole or skull fracture. Other applications include treatment of increased intracranial pressure following traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, and/or seizure. The heads positioned on the inner and outer surface of the skull and bone flap connected by a spring not only approximate the bone flap to the skull but can also allow external movement of the bone flap relative to the skull in case of an increased intracranial pressure. The external movement of the bone flap increases the intracranial space to accommodate the increase in intracranial pressure and provides for a decompressive craniectomy. Following normalization of the intracranial pressure, the bone flap is compressed back towards the skull by the spring or the elastomeric band and the two heads. In cases of re-operation requiring removal of the bone flap, the cranial fixation device described in the various embodiments can be removed by simply distracting the two heads apart by pulling the head on the outer surface either manually or with an instrument. While the current invention along with its various preferred embodiments are described and illustrated above, it is obvious that any variations made to the embodiments by those skilled in the art maintain the broad incentive concepts described herein.

What is claimed is:

1. A method of fixing skull bones using a fixation device comprising: two heads connected by a flexible component; one head configured to be positioned on outer surface of the skull and the other head on inner surface of the skull; the flexible component connecting the two heads providing a compressive force; the head configured to be positioned on the outer surface of the skull comprising of a mechanism for engaging an elongated instrument to maintain the flexible component and two heads in a distracted position until implantation, wherein said mechanism in the head configured to be positioned on the outer surface of the skull comprises an opening to allow for placement of the elongated instrument to maintain the two heads in a distracted position, wherein said elongated instrument and said head opening comprise of various corresponding configurations providing said distracted position of the two heads when the instrument is in place and removal of the instrument releasing the distracted position.

2. The method of claim 1, wherein said elongated instrument and said head opening comprising of partial threads maintaining said distracted position of the two heads while engaged with the said instrument in place and removal of the instrument by rotation releasing the distracted position.

3. The method of claim 1, wherein the said flexible component comprises one of the following: spring, elastomeric band, elastomeric cord.

4. The method of claim 1, wherein said mechanism for engaging an instrument on the head positioned on the outer surface of the skull comprises an opening with a ridge capable of engaging with a notch on the said instrument.

5. The method of claim 1, wherein the said heads are selected from a group of head segments of various size and configuration.

6. The method of claim 5, wherein the said head configuration being one of the following: circular, oval, rectangular, square, semi-circular, semi-oval, C-shape, L-shape, T-shape, X-shape, Y-shape, Z-shape, fan shaped.

7. The method of claim 1, wherein the said heads cover at least a portion of a burr hole or skull opening.

8. The method of claim 1, wherein the fixation device being made of a physiological compatible substance comprising of one or more of the following: bio-absorbable material, radiolucent material, metal, plastic, bone, elastomer, nitinol.

9. A method of fixing skull bones using a fixation device comprising: a first head and a second head coupled with a flexible component; positioning the first head on outer surface of the skull and the second head on inner surface of the skull; the first head on the outer surface of the skull comprising an opening for engaging an elongated instrument to maintain the flexible component between the first and second head in a distracted position; removing the elongated instrument by disengaging the said instrument from the opening on the first head after implantation to the skull, thereby allowing for contraction of the flexible component and approximation of the two heads.

10. The method of claim 9, wherein the said flexible component comprises a spring.

11. The method of claim 9, wherein the said opening on the first head also comprises of one or more ridges that engage with corresponding notches on the said elongated instrument.

12. The method of claim 9, wherein the said opening on the first head comprises of threads that engage with threads on the said elongated instrument.

13. The method of claim 9, wherein the said disengaging the instrument from the first head is achieved by rotation of the elongated instrument.

14. The method of claim 9, wherein the said first and/or second head comprise of spikes or a ridge to secure to the skull.

15. The method of claim 9, where in the said heads are selected from a group of head segments of various size and configuration.

16. The method of claim 15, wherein the said head configuration being one of the following: circular, oval, rectangular, square, semi-circular, semi-oval, C-shape, L-shape, T-shape, X-shape, Y-shape, Z-shape, fan shaped.

17. The method of claim 9, wherein the said heads cover at least a portion of a burr hole or skull opening.

18. The method of claim 9 wherein the said fixation device being made of a physiological compatible substance comprising of one or more of the following: bio-absorbable material, radiolucent material, metal, plastic, bone, elastomer, nitinol.

19. A method of fixing skull bones with a fixation device comprising of two heads connected by a spring; one head configured to covering outer surface of the skull and the other head configured to covering inner surface of the skull; maintaining the said heads in a distracted position prior to fixation through an elongated instrument with a locking mechanism; removing the elongated instrument by disengaging the locking mechanism to allow the spring connecting the two heads to provide a compressive force and place the heads in a retracted position, wherein the said locking mechanism comprises an opening on the head at the outer surface of the skull that engages with a corresponding notch on the said elongated instrument.

20. The method of claim 19, wherein the said elongated instrument comprises one of the following shapes: T-shape, L-shape, I-shape, Y-shape, P-shape, a knob or handle at the head of the instrument.

21. The method of claim 19, wherein the said disengaging the instrument from the head on the outer surface of the skull is achieved by rotation of the elongated instrument.

22. The method of claim 19, wherein the heads comprise of spikes or a ridge to secure to the skull.

23. The method of claim 19, wherein the said head configuration being one of the following: circular, oval, rectangular, square, semi-circular, semi-oval, C-shape, L-shape, T-shape, X-shape, Y-shape, Z-shape, fan shaped.

* * * * *